(12) United States Patent
Palermo

(10) Patent No.: US 7,915,044 B2
(45) Date of Patent: Mar. 29, 2011

(54) ELECTROFUSION MICROELECTRODE AND METHODS OF USING IT TO MANIPULATE CELLS AND/OR CELLULAR COMPONENTS

(75) Inventor: Gianpiero D. Palermo, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 178 days.

(21) Appl. No.: 11/315,475

(22) Filed: Dec. 22, 2005

(65) Prior Publication Data

US 2007/0148757 A1 Jun. 28, 2007

(51) Int. Cl.
*C12M 1/42* (2006.01)
*C12N 15/02* (2006.01)
(52) U.S. Cl. .......... 435/450; 435/286.5; 435/285.2; 435/461; 435/173.6
(58) Field of Classification Search .......... None
See application file for complete search history.

(56) References Cited

U.S. PATENT DOCUMENTS

| | | | |
|---|---|---|---|
| 4,371,273 A | 2/1983 | Kendall et al. | |
| 4,441,972 A | 4/1984 | Pohl | |
| 4,923,814 A | 5/1990 | Marshall, III | |
| 5,007,995 A | 4/1991 | Takahashi et al. | |
| 5,128,257 A | 7/1992 | Baer | |
| 5,185,922 A | 2/1993 | Pendley et al. | |
| 5,304,120 A | 4/1994 | Crandell et al. | |
| 5,304,486 A | 4/1994 | Chang | |
| 5,505,728 A | 4/1996 | Ellman et al. | |
| 5,589,047 A | 12/1996 | Coster et al. | |
| 5,650,305 A | 7/1997 | Hui et al. | |
| 5,749,837 A | 5/1998 | Palermo et al. | |
| 5,827,736 A | 10/1998 | Heller et al. | |
| 5,859,327 A | 1/1999 | Dev et al. | |
| 5,983,131 A | 11/1999 | Weaver et al. | |
| 5,993,434 A | 11/1999 | Dev et al. | |
| 6,001,617 A | 12/1999 | Raptis | |
| 6,009,345 A | 12/1999 | Hofmann | |
| 6,077,261 A | 6/2000 | Behl et al. | |
| 6,150,148 A | 11/2000 | Nanda et al. | |
| 6,261,815 B1 | 7/2001 | Meyer | |
| 6,347,247 B1 | 2/2002 | Dev et al. | |
| 6,355,485 B1 | 3/2002 | Jaroszeski et al. | |
| 6,452,564 B1 * | 9/2002 | Schoen et al. ........ | 343/872 |
| 7,101,703 B2 | 9/2006 | Palermo | |
| 7,186,547 B2 * | 3/2007 | Palermo ........ | 435/285.2 |
| 2002/0010414 A1 | 1/2002 | Coston et al. | |
| 2002/0019035 A1 | 2/2002 | Tai et al. | |
| 2007/0148758 A1 | 6/2007 | Palermo | |

OTHER PUBLICATIONS

Stromburg et al., "Manipulating the Genetic Identity and Biochemical Surface Proteins of Individual Cells with Electric-Field-Induced Fusion," PNAS 97(1):7-11 (2000).
Stromburg et al., "Microfluidic Device for Combinatorial Fusion of Liposomes and Cells," Anal. Chem. 73:126-130 (2001).
Rae et al., "Instrument and Techniques Single-Cell Electrroporation," Pflugers Archiv-European Journal of Physiology (2001).
Haas et al., "Single-Cell Electroporation for Gene Transfer In Vivo," Neuron 29:583-591 (2001).
Webster's Ninth New Collegiate Dictionary, pp. 470-471, 1983.
Takeuchi et al., "A Reliable Technqiue of Nuclear Transplantation for Immature Mammalian Oocytes," Human Reproduction 14:1312-1317 (1999).
International Search Report for International Patent Application No. PCT/US06/44394 (Feb. 19, 2008).

* cited by examiner

*Primary Examiner* — James S Ketter
(74) *Attorney, Agent, or Firm* — LeClairRyan

(57) ABSTRACT

The present invention relates to an electrofusion microelectrode made of a tube having a first proximal end and a second distal end. The tube has an electrically conductive coating on its exterior surface that extends continually from the first proximal end of the tube toward the second distal end of the tube. Also disclosed is an electrofusion microelectrode unit having an electrofusion microelectrode and a holding tool capable of receiving the electrofusion microelectrode at the second distal end of the tube. The present invention also relates to a system having two or more electrofusion microelectrodes of the present invention and to methods of manipulating cells and/or cellular components using the electrofusion microelectrodes, units, and systems of the present invention.

32 Claims, 5 Drawing Sheets

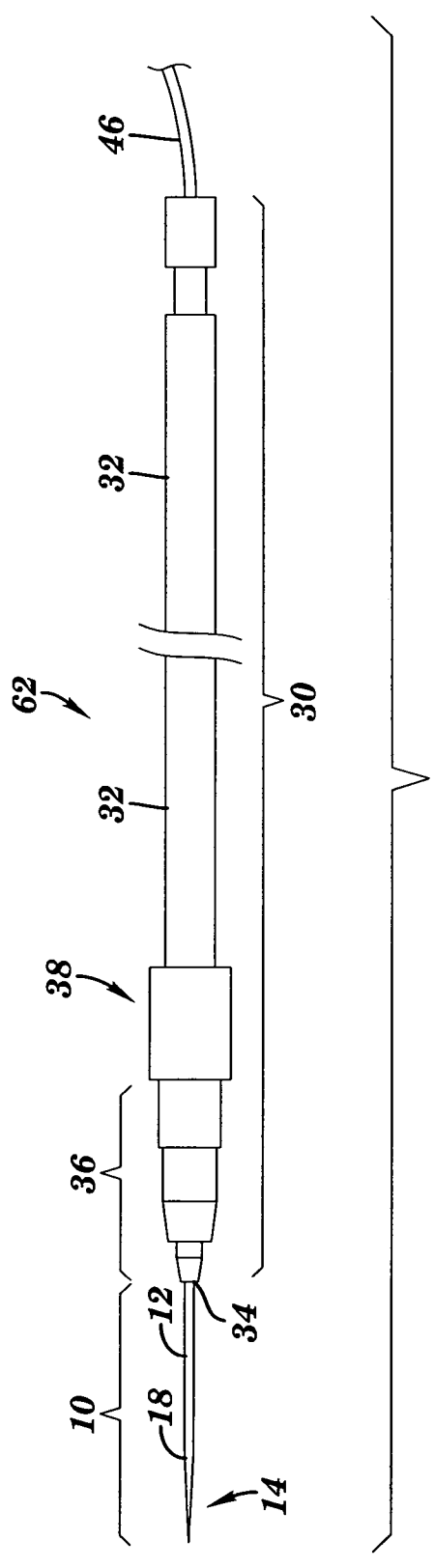
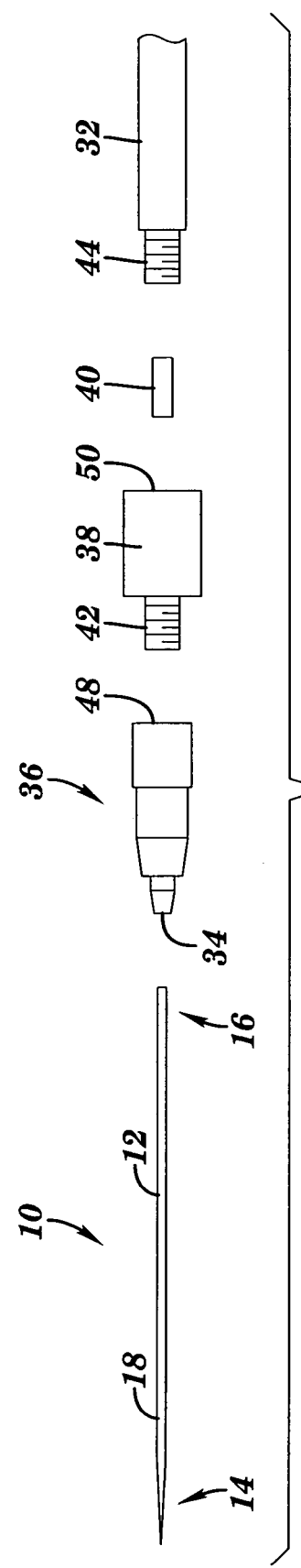
FIG. 3A
FIG. 3B

US 7,915,044 B2

ELECTROFUSION MICROELECTRODE AND METHODS OF USING IT TO MANIPULATE CELLS AND/OR CELLULAR COMPONENTS

FIELD OF THE INVENTION

The present invention relates to an electrofusion microelectrode and methods of using it to manipulate cells and/or cellular components.

BACKGROUND OF THE INVENTION

Electrofusion and electroporation of cells involves application of an electrical current to the cells. In many instances, it is desirable to align cells prior to applying a direct electrical current. Alignment of cells may be carried out manually by aspiration or vacuum suction. Alignment of cells may also be performed by applying an alternate electrical current. However, when alignment is performed by applying alternate current, cell survival is drastically reduced. Therefore, it would be desirable to have a tool that has a dual capacity to manually align cells and deliver a direct electrical current.

Cell fusion procedure involves localized reversible permeabilization of the cell membrane, which can be induced by applying a pulse or pulses of direct current (DC). It is well known when electrofusing cells, that application of the dielectrophoretic alternating current (AC) for cell alignment prior to administration of the DC pulse greatly improved the rate of cell fusion. The application of AC is necessary for alignment and orientation of the cells in relation to the medium's volume and the distance between the two electrodes. The AC, however, is also known to be deleterious to the cell and at high voltage and/or extensive periods of time is even responsible for cell lysis. Moreover, the typical construction of the chamber is designed so that a large number of cells can be fused at one time. Because of the large volume of medium needed, specific low conductivity solutions are required whose antioxidant components can also harm the cell or, in the specific case of the oocyte, even induce cell activation. An alternative to the existing chamber approach, to avoid the use of antioxidants and the AC at once, is to execute the individual cell alignment manually under dissecting microscopy.

In summary, for conventional electrofusion methods, the disadvantages can be summarized in the requirement for: i) a non-electrolyte solution that is obviously not physiological and can impair cell viability; ii) due to the large inter-electrode distance, the passage of AC pulses can induce thermal damage with consequent cell distress; iii) individual cell alignment is time-consuming; and iv) the electric chamber can be a source of pathogenic contamination due to its repetitive use.

The present invention is directed to overcoming these and other deficiencies in the art.

SUMMARY OF THE INVENTION

One aspect of the present invention relates to an electrofusion microelectrode made of a tube having a first proximal end and a second distal end. The tube has an electrically conductive coating on its exterior surface that extends continually from the first proximal end of the tube to the second distal end of the tube.

Another aspect of the present invention relates to an electrofusion microelectrode unit containing an electrofusion microelectrode as described above and a holding tool capable of receiving the electrofusion microelectrode at the second distal end of the tube.

A further aspect of the present invention relates to a system containing two or more electrofusion microelectrode units as described above.

Yet another aspect of the present invention relates to a method of manipulating cells and/or cellular components. This method involves contacting a cell and/or cellular component with the first proximal end of the tube of the electrofusion microelectrode as described above. Such contacting is carried out under conditions effective to manipulate the cell and/or cellular component.

Still another aspect of the present invention relates to a method of manipulating cells and/or cellular components. This method involves contacting a cell and/or cellular component with two or more electrofusion microelectrodes as described above. Contacting a cell and/or cellular component is carried out at the first proximal end of each microelectrode tube under conditions effective to manipulate the cell and/or cellular component.

The present invention provides a tool having the dual capacity to manually align cells and deliver direct current to cells.

Mammalian nuclear transfer is dedicated to a small number of cells, particularly when dealing with human oocytes. Therefore, the availability of a tool that allows individual cell alignment would be ideal. The use of individual microelectrodes, under micromanipulation control, permit pinpointing the desired orientation of the cell to be fused and because of the direct electrode-cell contact, can bypass the use of alternating current and the adoption of a small amount of medium. The omission of alternating current together with the small volume required, allows the employment of a routine culture medium that can be covered with oil. Further, the direct cell contact would even reduce the amount of direct current to be administered, decreasing chance of thermal damage to the cell. Finally, the limited cost of this microelectrode makes it disposable, thereby eliminating the chances of contamination.

BRIEF DESCRIPTION OF THE DRAWINGS

In FIG. 1A, the microelectrode tube has a holding pipette configuration where the first proximal end is straight. In FIG. 1B, the microelectrode tube has a holding pipette configuration where the first proximal end is bent.

In FIG. 2A, the first proximal end of the microelectrode tube is straight and open. In FIG. 2B, the first proximal end of the microelectrode tube is straight and sealed. In FIG. 2C, the first proximal end of the microelectrode tube is bent and open. In FIG. 2D, the first proximal end of the microelectrode tube is bent and sealed.

FIG. 3A is a plan view of one embodiment of the electrofusion microelectrode unit of the present invention. The electrofusion microelectrode unit contains an electrofusion microelectrode of the present invention, which is positioned in a holding tool. As shown, the holding tool receives the electrofusion microelectrode at the second distal end of the microelectrode tube. FIG. 3B is an exploded view of the electrofusion microelectrode unit illustrated in FIG. 3A.

DETAILED DESCRIPTION OF THE INVENTION

One aspect of the present invention relates to an electrofusion microelectrode made of a tube having a first proximal end and a second distal end. The tube has an electrically conductive coating on its exterior surface that extends continually from the first proximal end of the tube to the second distal end of the tube.

Figure 1A:
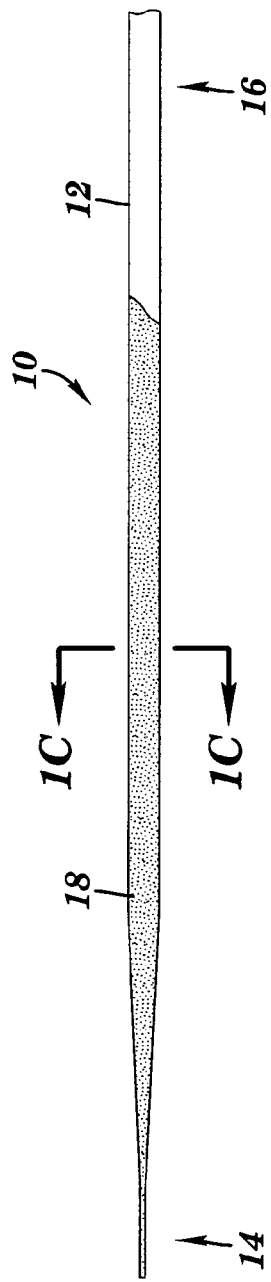
FIGS. 1A-B are plan views of two different embodiments of the electrofusion microelectrode of the present invention. The electrofusion microelectrodes of FIGS. 1A-B are made of a tube having a first proximal end and second distal end, with an electrically conductive coating on the exterior surface of the tube that extends continually from the first proximal end of the tube to the second distal end of the tube.
Figure 1B:
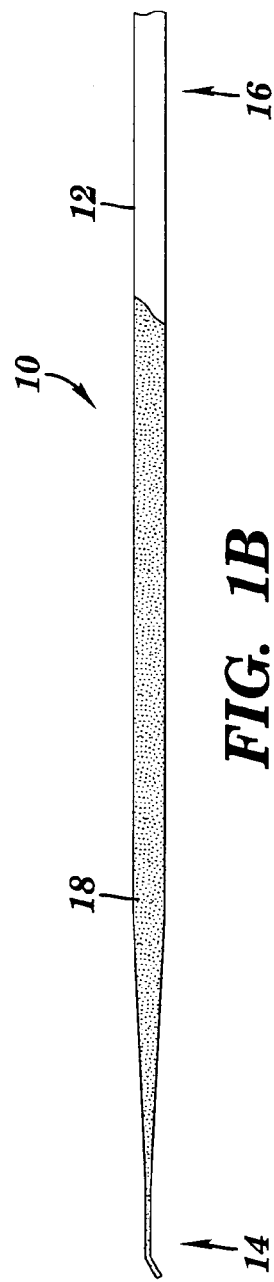

FIGS. 1A-B show two different embodiments of the electrofusion microelectrode of the present invention. As illustrated, electrofusion microelectrode 10 is made of microelectrode tube 12 having proximal end 14 (the electrode tip) and distal end 16. Electrically conductive coating 18 on the exterior surface of tube 12 extends continually from proximal end 14 of tube 12 toward distal end 16. In the embodiment shown in FIG. 1A, microelectrode tube 12 has a holding pipette configuration where proximal end 14 is straight. In the embodiment shown in FIG. 1B, microelectrode tube 12 has a holding pipette configuration where proximal end 14 is bent.

Tube 12 of electrofusion microelectrode 10 may be any hollow casing with various geometric conformations. Thus, if desired, the walls of tube 12 may be angled. In a preferred embodiment, tube 12 is cylindrical. Even more preferably, tube 12 has a holding pipette configuration.

The diameter and length of tube 12 can, of course, vary. As discussed in greater detail below, the diameter and length of tube 12 will vary according to the type of cells (and/or cellular components) and the type of manipulation for which electrofusion microelectrode 10 is used. Typically, tube 12 is about 50 to 80 millimeters in length, and has a diameter of about 0.5 to 1.5 millimeters.

Tube 12 of microelectrode 10 may be made of any number of materials including, but not limited to, glass, plastic, PVC, ceramic, and/or metal. In a preferred embodiment, tube 12 is made of glass. Even more preferably, tube 12 is made of a borosilicate glass capillary tube, pulled and forged into a holding pipette configuration.

Figure 1C:
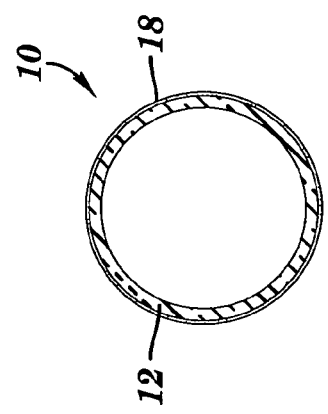
FIG. 1C is a cross-sectional view of the electrofusion microelectrode of FIG. 1A, illustrating how the electrically conductive coating can extend circumferentially around the microelectrode tube.

Electrically conductive coating 18 is preferably applied in liquid form by painting it onto the exterior surface of tube 12. In a preferred embodiment illustrated in FIG. 1C, electrically conductive coating 18 extends circumferentially around microelectrode tube 12. Suitable electric conductors include, without limitation, aluminum, copper, silver, gold, titanium, platinum, tungsten, and alloys and mixtures thereof.

Figure 2A:
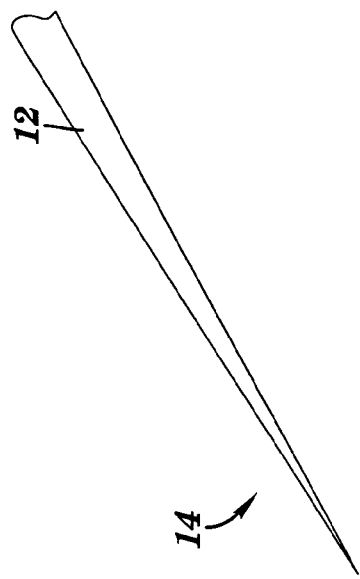
FIGS. 2A-D are perspective views showing various embodiments of the first proximal end of the electrofusion microelectrode tube of the present invention.
Figure 2B:
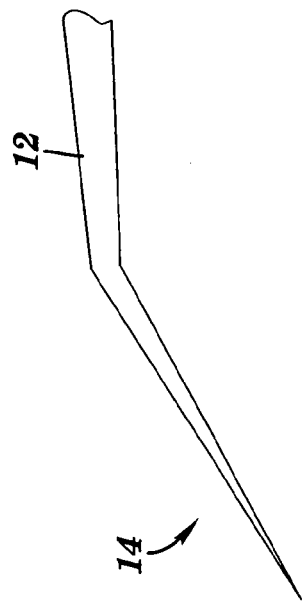
Figure 2C:
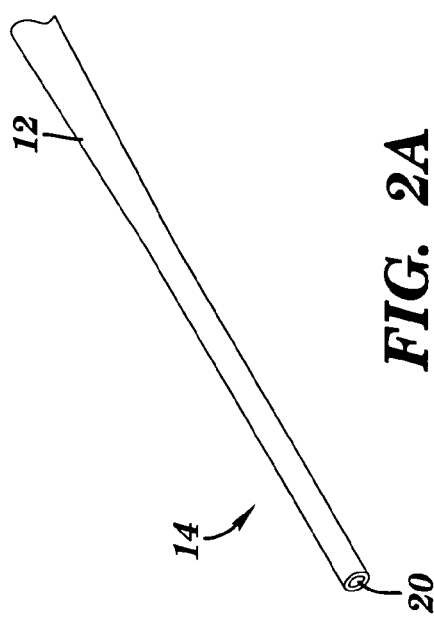
Figure 2D:
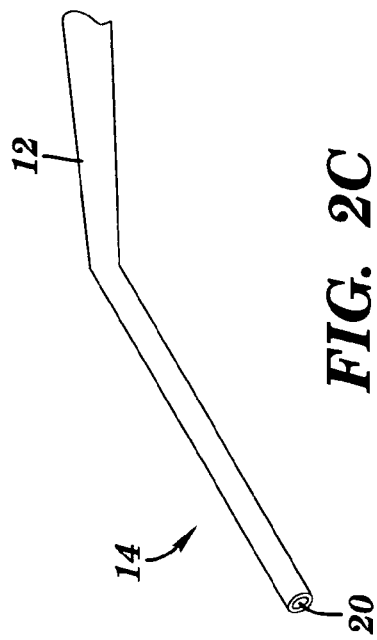

Proximal end 14 of microelectrode tube 12 may take on various configurations. In one embodiment (FIGS. 2A-B), proximal end 14 of tube 12 is straight. In an alternative embodiment (FIGS. 2C-D), proximal end 14 of tube 12 is bent. When proximal end 14 of tube 12 is bent, the bend is preferably about 0 to 90 degrees from the tip of proximal end 14. Proximal end 14 of tube 12 may also be either open (FIGS. 2A and 2C, opening 20) or sealed (FIGS. 2B and 2D) at the tip.

Another aspect of the present invention relates to an electrofusion microelectrode unit having an electrofusion microelectrode as described above and a holding tool capable of receiving the electrofusion microelectrode at the second distal end of the microelectrode tube.

FIG. 3A illustrates one embodiment of an electrofusion microelectrode unit of the present invention. As shown, electrofusion microelectrode unit 62 has electrofusion microelectrode 10 positioned in holding tool 30, with proximal end 14 of electrofusion microelectrode 10 protruding out of holding tool 30.

Holding tool 30 is a tube containing receiving component 36, which contains orifice 34 through which electrofusion microelectrode 10 is received. Holding tool 30 also has main shaft 32 and electrical insulator 38, which is position between receiving component 36 and main shaft 32, whereby electric current passing through receiving component 36 does not reach main shaft 32.

Receiving component 36 and main shaft 32 may be constructed of the same material and, preferably, are constructed of a durable material that is electrically conductive. On the other hand, electrical insulator 38 is constructed of a material that does not conduct electricity, such as a plastic material. The electrically non-conductive properties of electrical insulator 38 prevent electric current from passing through receiving component 36 into main shaft 32. This design creates a more localized electrical effect in performing electro-manipulation procedures, discussed in greater detail below. The insulating properties of electrical insulator 38 also permits suction of cells into holding tool 30 with minimized cell death.

FIG. 3B is an exploded view of electrofusion microelectrode unit 62 of FIG. 3A, which shows the assembly of holding tool 30. As illustrated, the three main components of holding tool 30 (receiving component 36, electrical insulator 38, and main shaft 32) are connected by means of threaded connector 42 on electrical insulator 38 and threaded connector 44 on main shaft 32. Threaded connector 42 can be fastened into opening 48, which has threaded walls matching the threads of threaded connector 42. Likewise, threaded connector 44 can be fastened into opening 50, which has threaded walls matching the threads of threaded connector 44. This particular assembly prevents the electrically conductive material of receiving component 36 from coming into electrical contact with the electrically conductive material of main shaft 32.

Insulating sleeve 40 is fitted over distal end 16 of tube 12 to prevent unwanted movement of tube 12 when it is positioned in holding tool 30 and to further insulate holding tool 30 when electrical current is applied to electrically conductive coating 18.

Microelectrode 10 is positioned in holding tool 30 by sliding tube 12 (via distal end 16) into orifice 34 of receiving component 36. In a preferred embodiment, microelectrode 10 is positioned far enough into receiving component 36 for receiving component 36 to clamp down on microelectrode 10.

Referring again to FIG. 3A, according to one embodiment, first proximal end 14 of tube 12 is open (FIGS. 2A and 2C) and electrofusion microelectrode unit 62 is operably connected to a vacuum or aspirator. Preferably, the vacuum or aspirator is operably connected to microelectrode tube 12 at its distal end. Connection of a vacuum or aspirator to microelectrode tube 12 is preferably achieved by connection hose 46. As illustrated in FIG. 3A, connection hose 46 is positioned in main shaft 32 of holding tool 30 where it draws a vacuum on the interior of microelectrode tube 12 and opening 20.

Figure 4:
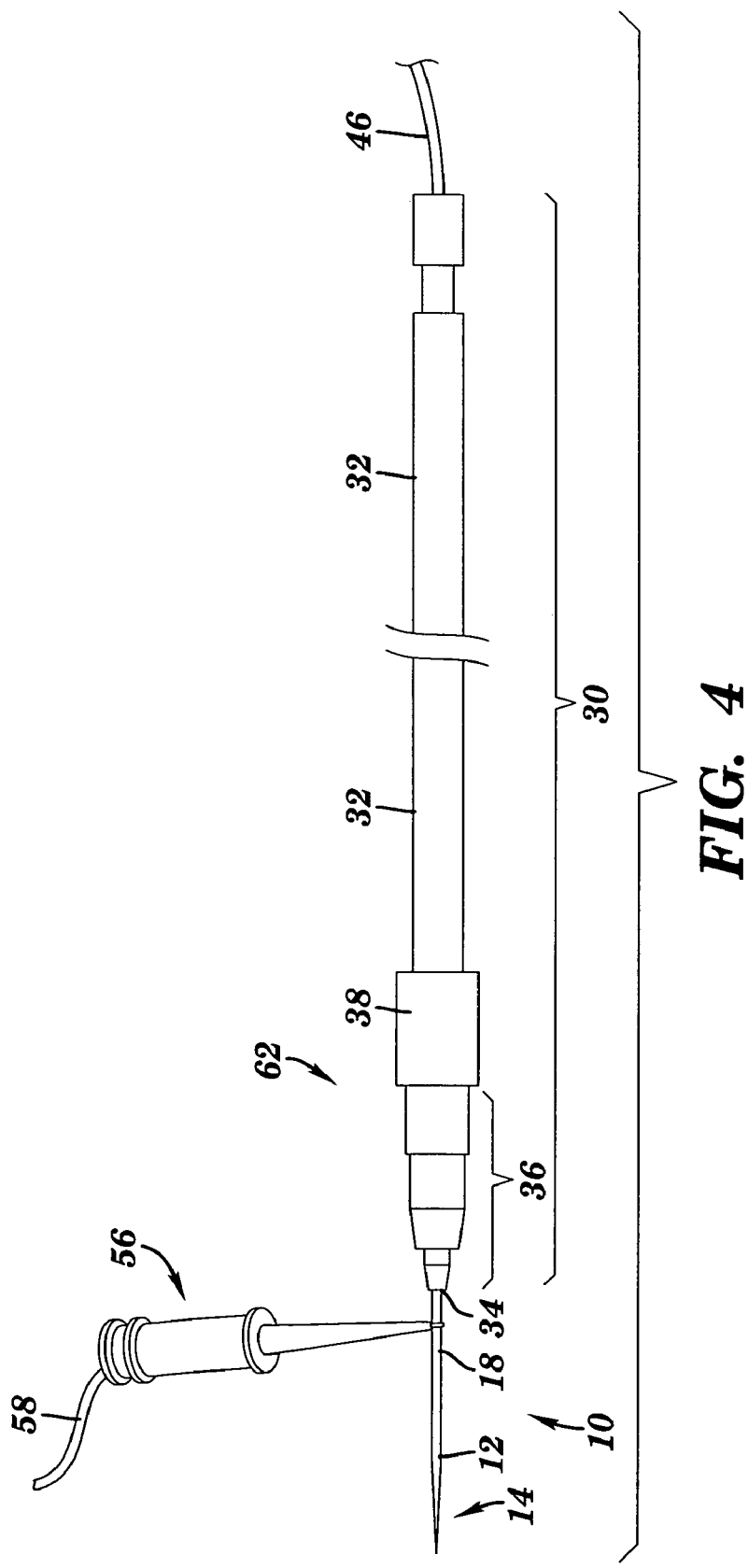
FIG. 4 is a plan view of one embodiment of the electrofusion microelectrode unit of the present invention having an electrofusion microelectrode of the present invention positioned in a holding tool. An electrode clip operably connected to an electrical power source is attached to the electrofusion microelectrode at the electrically conductive coating.

According to another embodiment illustrated in FIG. 4, electrofusion microelectrode unit 62 has electrode clip 56 attached to microelectrode tube 12 at electrically conductive coating 18. Electrode clip 56 preferably attaches to microelectrode tube 12 by clamping onto microelectrode tube 12 near orifice 34. Electrode clip 56 is connected to an electrical power source via electrical connectors 58. According to this embodiment, current passes from the power source to tube 12 through electrode clip 56.

In a preferred embodiment, the electrofusion microelectrode unit of the present invention is mounted onto a micromanipulator. Preferably, the micromanipulator is used under inverted microscopy. Suitable micromanipulators include, but are not limited to, the MM188 and MM109 micromanipulators manufactured by Narishigie Co., LTD (Tokyo, Japan).

More than one electrofusion microelectrode or microelectrode unit of the present invention may be used together. Thus, another aspect of the present invention relates to a system containing two or more electrofusion microelectrodes of the present invention.

Figure 5:
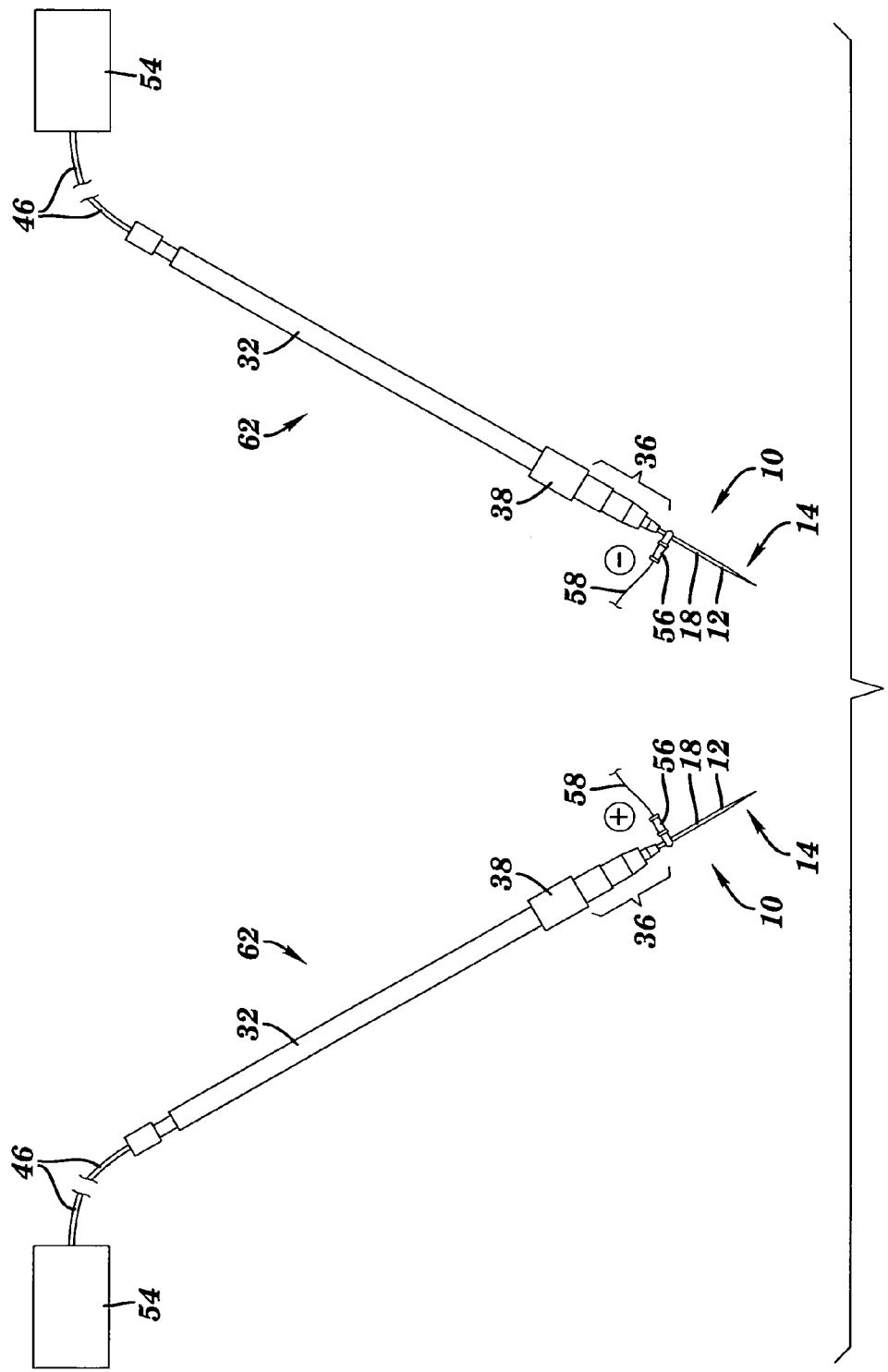
FIG. 5 illustrates one embodiment of the system of the present invention. The system has two electrofusion microelectrode units of the present invention operably connected to vacuums or aspirators, with each electrofusion microelectrode being further equipped with an electrode clip operably connected to an electrical power source.

FIG. 5 illustrates one embodiment of the system of the present invention containing two electrofusion microelectrode units 62, each operably connected to vacuum or aspirator 54. In addition, electrofusion microelectrodes 10 are in electrical contact with electrode clips 56, which are operably connected to an electrical power supply via connectors 58. In a preferred embodiment of the system, a first electrofusion microelectrode unit of the present invention is connected to a first electrode clip 58 which is connected to the positive terminal of a direct current power source and a second electrofusion microelectrode unit of the present invention is connected to a second electrode clip 58 which is connected to the negative terminal of a direct current power source.

In operation, the electrofusion microelectrode, unit, and system of the present invention can be used to manipulate cells and/or cellular components. Thus, another aspect of the present invention relates to a method of manipulating cells and/or cellular components. This method involves contacting a cell and/or cellular component with an electrofusion microelectrode of the present invention. Contacting a cell and/or cellular component with an electrofusion microelectrode of the present invention is carried out at the first proximal end of the microelectrode tube under conditions effective to manipulate the cell and/or cellular component.

A further aspect of the present invention relates to a method of manipulating cells and/or cellular components. This method involves contacting a cell and/or cellular component with two or more electrofusion microelectrodes of the present invention. Contacting a cell and/or cellular component is carried out at the first proximal end of each microelectrode tube under conditions effective to manipulate the cell and/or cellular component.

Manipulation of cells pursuant to the methods of the present invention may involve aligning, fusing, electroporating, electrofusing, and/or transplanting cells and/or cellular components.

According to one embodiment of the methods of the present invention, manipulation of cells and/or cellular components is carried out with an electrofusion microelectrode of the present invention, where the first proximal end is open and where the electrofusion microelectrode has a vacuum or aspirator operably connected to the microelectrode at the second distal end of the tube. According to this embodiment, contacting the cell and/or cellular component is carried out by applying aspiration or suction to the cell and/or cellular component.

Aspiration or suction is typically applied to cells and/or cellular components pursuant to the method of the present invention for the purpose of manually aligning cells and/or cellular components. Manual alignment of cells by suction or aspiration according to this method avoids the use of alternate current for alignment, which significantly improves cell survival. Drastic improvement in cell survival permits lower cell numbers to be used in each manipulation.

A combination of microelectrode motion and aspiration or suction may be used in carrying out the methods of the present invention. Generally, it is preferable to align cells using aspiration or suction and then apply direct current via the electrofusion microelectrode of the present invention.

Nuclear transplantation is particularly amenable to the methods of the present invention. Nuclear transplantation is carried out using the electrofusion microelectrode, unit, or system of the present invention by removing a nucleus from a first oocyte and transplanting the nucleus into the perivitelline space of a second, previously enucleated oocyte, and then integrating the transplanted nucleus of the first oocyte with the cytoplasm of the second oocyte. This is achieved by delivering a direct current to the nucleus and cytoplasm.

As discussed above, the length and diameter of the electrofusion microelectrode may vary according to the type of cells and type of manipulation for which the microelectrode is used. For example, when used for nuclear transplantation of mammalian cells, a tube diameter in the range of from about 15 µm to about 25 µm is preferred. When used for mammalian cell fusion, a tube diameter in the range of from about 60 µm to about 100 µm is preferred. In one embodiment, the outer diameter of the tube may be about 0.97 mm while the inner diameter of the tube may be about 0.69 mm. In this embodiment, the tube is quite thin walled, having a thickness of only about 0.28 mm.

EXAMPLES

The following examples are provided to illustrate embodiments of the present invention but are by no means intended to limit its scope.

Example 1

Construction of Electrofusion Microelectrode

A capillary tube, 78 mm in length, and having an outer diameter of 0.97 mm and an inner diameter of 0.69 mm (Drummond Scientific, Boomall, Pa.), is pulled on a horizontal microelectrode puller (micropuller) (Campden Inc., LTD., London) approximately 60 to 100 µm at a location of 10-15 mm from one end (proximal end). The tube is cut and fine polished on a microforge (Narishige Co., LTD, Tokyo, Japan) to obtain a final outer diameter of 60 µm and an inner diameter of 20 µm.

Example 2

Nuclear Transplantation for Immature Mammalian Oocytes

Germinal vesicle (GV) stage oocytes are retrieved by puncturing follicles of unstimulated ovaries of B6D2F1 female mice. A karyoplast is then removed by micromanipulation using one or more of the subject electrofusion microelctrodes in a medium supplemented with cytochalasin B. One karyoplast is subsequently introduced into the perivitelline space of a previously enucleated immature oocyte. Each grafted oocyte is then positioned between two electrofusion microelectrodes of the present invention and exposed to a single or double 1.0 kV/cm, 50-99 µs direct current fusion pulse(s). Thirty to 60 minutes later, the oocytes are examined for sign of fusion. The restored oocytes are then placed in culture and assessed for maturation. Oocytes which have extruded a first polar body may be fixed and stained with Giemsa for chromosome analysis. As controls, approximately one third of oocytes are not subjected to any manipulation, but are merely cultured in the same media and exposed to the same reagents.

Example 3

Germinal Vesicle Transplantation

Germinal vesicle (GV) stage oocytes are retrieved by puncturing follicles of unstimulated ovaries of B6D2F1 female mice. Metaphase II (MII) oocytes are collected 15 hours after hCG injection of PMSG stimulated females. Karyoplasts are then removed from GV oocytes using one or more subject electrofusion microelectrodes, in a medium supplemented with cytochalsin B. MII oocytes are enucleated by removing the "hub" area where the metaphase spindle is located, together with the first polar body using one or more of the subject electrofusion microelectrodes. A GV karyoplast is subsequently introduced into the perivitelline space of either a previously enucleated immature (GV) or a mature (MII) oocyte. Each of these manipulated oocytes is then positioned between two of the subject electrofusion microelectrodes and exposed to a single or double 1.0 kV/cm, 50-99 µs direct current fusion pulse(s) for electrofusion. The oocytes that show signs of fusion 30 to 60 minutes later are then placed in culture for 12 hours, to allow nuclear maturation. Oocytes which extrude the first polar body may be fixed and stained with Giemsa for chromosome analysis.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An electrofusion microelectrode comprising:
    a tube having a holding pipette configuration with first proximal end and a second distal end, wherein the tube has an electrically conductive coating on its exterior surface, said coating extending continually from the first proximal end of the tube to the second distal end of the tube.

2. The electrofusion microelectrode according to claim 1, wherein the first proximal end of the tube is bent.

3. The electrofusion microelectrode according to claim 1, wherein the tube is made of a material selected from the group consisting of glass, plastic, PVC, ceramic, and metal.

4. The electrofusion microelectrode according to claim 3, wherein the tube is made of glass.

5. The electrofusion microelectrode according to claim 1, wherein the electrically conductive coating is selected from the group consisting of aluminum, copper, silver, gold, titanium, platinum, tungsten, alloys, and mixtures thereof.

6. The electrofusion microelectrode according to claim 1, wherein the electrically conductive coating extends circumferentially around the tube.

7. An electrofusion microelectrode unit comprising:
    an electrofusion microelectrode according to claim 1 and
    a holding tool capable of receiving the electrofusion microelectrode at the second distal end of the tube.

8. The electrofusion microelectrode unit according to claim 7, wherein the first proximal end of the tube is open, said electrofusion microelectrode unit further comprising:
    a vacuum or aspirator operably connected to the microelectrode at the second distal end of the tube, whereby suction is drawn on the first proximal end.

9. The electrofusion microelectrode unit according to claim 7 further comprising:
    an electrode clip operably connected to an electrical power source and attachable to the tube at the electrically conductive coating, whereby current can pass from the power source to the tube through the electrode clip.

10. The electrofusion microelectrode unit according to claim 7, wherein the holding tool further comprises:
    a tube comprising:
        a receiving component, into which the second distal end of the microelectrode tube is received;
        a main shaft; and
        an electrical insulator positioned between the receiving component and the main shaft, whereby electrical current passing through the receiving component does not reach the main shaft.

11. The electrofusion microelectrode unit according to claim 7 further comprising:
    a micromanipulator positioned to control the holding tool.

12. A system comprising:
    two or more electrofusion microelectrode units according to claim 7.

13. A method of manipulating cells and/or cellular components, said method comprising:
    contacting a cell and/or cellular component with the first proximal end of the tube of the electrofusion microelectrode according to claim 1, under conditions effective to manipulate the cell and/or cellular component.

14. The method according to claim 13, wherein the first proximal end of the tube is open, and said electrofusion microelectrode further comprises a vacuum or aspirator operably connected to the microelectrode at the second distal end of the tube, said method further comprising:
    applying suction to the cell and/or cellular component during said contacting.

15. The method according to claim 13, wherein said electrofusion microelectrode further comprises an electrode clip operably connected to an electrical power source and attachable to the tube at the electrically conductive coating, said method further comprising:
    applying an electrical current to the cell and/or cellular component during said contacting.

16. The method according to claim 13, wherein said contacting comprises:
    aligning, fusing, electroporating, electrofusing, and/or transplanting cells and/or cellular components.

17. A method of manipulating cells and/or cellular components, said method comprising:
    contacting a cell and/or cellular component with two or more electrofusion microelectrodes according to claim 1, wherein said contacting is carried out at the first proximal end of the tubes under conditions effective to manipulate the cell and/or cellular component.

18. An electrofusion microelectrode comprising:
    a tube having a first proximal end which is sealed and a second distal end, wherein the tube has an electrically conductive coating on its exterior surface, said coating extending continually from the first proximal end of the tube to the second distal end of the tube.

19. The electrofusion microelectrode according to claim 18, wherein the first proximal end of the tube is bent.

20. The electrofusion microelectrode according to claim 18, wherein the tube is made of a material selected from the group consisting of glass, plastic, PVC, ceramic, and metal.

21. The electrofusion microelectrode according to claim 20, wherein the tube is made of glass.

22. The electrofusion microelectrode according to claim 18, wherein the electrically conductive coating is selected from the group consisting of aluminum, copper, silver, gold, titanium, platinum, tungsten, alloys, and mixtures thereof.

23. The electrofusion microelectrode according to claim 18, wherein the electrically conductive coating extends circumferentially around the tube.

24. An electrofusion microelectrode unit comprising:
an electrofusion microelectrode according to claim 18 and
a holding tool capable of receiving the electrofusion microelectrode at the second distal end of the tube.

25. The electrofusion microelectrode unit according to claim 24 further comprising:
an electrode clip operably connected to an electrical power source and attachable to the tube at the electrically conductive coating, whereby current can pass from the power source to the tube through the electrode clip.

26. The electrofusion microelectrode unit according to claim 24, wherein the holding tool further comprises:
a tube comprising:
a receiving component, into which the second distal end of the microelectrode tube is received;
a main shaft; and
an electrical insulator positioned between the receiving component and the main shaft, whereby electrical current passing through the receiving component does not reach the main shaft.

27. The electrofusion microelectrode unit according to claim 24 further comprising:
a micromanipulator positioned to control the holding tool.

28. A system comprising:
two or more electrofusion microelectrode units according to claim 24.

29. A method of manipulating cells and/or cellular components, said method comprising:
contacting a cell and/or cellular component with the first proximal end of the tube of the electrofusion microelectrode according to claim 18, under conditions effective to manipulate the cell and/or cellular component.

30. The method according to claim 29, wherein said electrofusion microelectrode further comprises an electrode clip operably connected to an electrical power source and attachable to the tube at the electrically conductive coating, said method further comprising:
applying an electrical current to the cell and/or cellular component during said contacting.

31. The method according to claim 29, wherein said contacting comprises:
aligning, fusing, electroporating, electrofusing, and/or transplanting cells and/or cellular components.

32. A method of manipulating cells and/or cellular components, said method comprising:
contacting a cell and/or cellular component with two or more electrofusion microelectrodes according to claim 18, wherein said contacting is carried out at the first proximal end of the tubes under conditions effective to manipulate the cell and/or cellular component.

* * * * *